United States Patent
Cudney

(10) Patent No.: US 10,258,252 B1
(45) Date of Patent: Apr. 16, 2019

(54) WOUND MEASUREMENT AND TRACKING SYSTEM AND METHOD

(71) Applicant: David Cudney, Shalimar, FL (US)

(72) Inventor: David Cudney, Shalimar, FL (US)

(*) Notice: Subject to any disclaimer, the term of this patent is extended or adjusted under 35 U.S.C. 154(b) by 190 days.

(21) Appl. No.: 15/237,132

(22) Filed: Aug. 15, 2016

Related U.S. Application Data

(60) Provisional application No. 62/232,091, filed on Sep. 24, 2015.

(51) Int. Cl.
*A61B 5/05* (2006.01)
*A61B 5/053* (2006.01)
*G16H 50/50* (2018.01)

(52) U.S. Cl.
CPC ............ *A61B 5/053* (2013.01); *A61B 5/0536* (2013.01); *G16H 50/50* (2018.01)

(58) Field of Classification Search
CPC .............................. A61B 5/053; A61B 5/0536
See application file for complete search history.

(56) References Cited

U.S. PATENT DOCUMENTS

| | | | | |
|---|---|---|---|---|
| 5,810,742 A * | 9/1998 | Pearlman | ............. | A61B 5/0536 600/547 |
| 6,678,552 B2 * | 1/2004 | Pearlman | ............. | A61B 5/0536 600/547 |
| 7,499,745 B2 * | 3/2009 | Littrup | ................... | A61B 5/053 600/547 |

* cited by examiner

*Primary Examiner* — Michael J D Abreu
(74) *Attorney, Agent, or Firm* — J. Nevin Shaffer, Jr.

(57) ABSTRACT

A wound measurement and tracking system includes a surface measurement indicator where the surface measurement indicator is configured to collect wound information from a wound. A transmitter device is provided that is connected with the surface measurement indicator and is configured to transmit wound information to a data processor. A tunneling depth indicator is provided where the tunneling depth indicator measures tunneling and undermining of the wound. A transmitter device is connected with the tunneling depth indicator that is configured to transmit tunneling and undermining information from the wound to a data processor. And a data processor is provided that is conformed to connect with both of the transmitter devices where the data processor includes data processing software configured for comparison and analysis of wound information.

17 Claims, 11 Drawing Sheets

WOUND MEASUREMENT AND TRACKING SYSTEM AND METHOD

CROSS REFERENCE TO RELATED APPLICATION

This application claims the benefit of previously filed U.S. provisional patent application No. 62/232,091 filed Sep. 24, 2015 for a "Wound Measurement and Tracking System and Method". The Applicant hereby claims the benefit of this provisional application under 35 U.S.C. § 119. The entire content of this provisional application is incorporated herein by this reference.

FIELD OF THE INVENTION

This invention relates to a wound measurement and tracking system and method. In particular, according to one embodiment, the present invention consists of a wound measurement and tracking system including a surface measurement indicator where the surface measurement indicator is configured to collect wound information from a wound. A transmitter device is provided that is connected with the surface measurement indicator and is configured to transmit wound information to a data processor. A tunneling depth indicator is provided where the tunneling depth indicator measures tunneling and undermining of the wound. A transmitter device is connected with the tunneling depth indicator that is configured to transmit tunneling and undermining information from the wound to a data processor. And a data processor is provided that is conformed to connect with both of the transmitter devices where the data processor includes data processing software configured for comparison and analysis of wound information.

BACKGROUND OF THE INVENTION

Chronic cutaneous wound complications account for an estimated $20 billion of health care costs annually in the U.S. Healing chronic wounds involves monitoring at specific intervals and changes to plan of care when needed. Monitoring the wound involves a series of measurements taken by a clinician. The collected wound data is then analyzed to determine the most effective plan of care. Patients, physicians or nurses are then able to make changes to the plan of care based on the analysis. This is an iterative process that typically takes place once or twice per week or as needed until the wound is healed. Inaccurate assessment leads to an ineffective plan of care which leads to higher health care costs, longer healing times, and in some cases loss of limbs or lives.

Through patient and subject matter expert consultation, Applicant has determined that the current wound assessment process is largely subjective, inconsistent, and inaccurate. Market research has indicated that there are currently no available processes, techniques, devices, or systems that fully meet the need for non-subjective, accurate, and consistent wound assessments. Through research, Applicant has determined that inaccurate assessment primarily stems from the subjectivity and inaccuracy of the measurement and analysis process that is currently used.

Applicant has categorized the current wound assessment process into two primary categories which include patient and wound specific data collection and data analysis.

Patient specific data collection involves collecting patient demographics, comorbidities, socioeconomic state, general nutritional state, and vital signs. Wound specific data collection involves collecting wound surface measurements, tunneling measurements, undermining measurements, tissue coloration, drainage coloration, drainage odor, and peri-wound tissue temperatures.

Data analysis involves comparing nominal measurements over time, associating tissue colorations and temperatures with various degrees of tissue health, associating drainage characteristics with various degrees of wound health, and associating patient specific information with symptoms that are present. Some of these analyses are performed at the patient bedside by the immediate care clinician during the wound assessment. Others are performed after the assessment by physicians or other wound care experts. Ultimately, it is the data analysis on which the most effective plan of care is based.

Nominal measurements of a wound typically include surface length, surface width, depth at deepest point, depth of undermining, extent of undermining, depth of tunneling, and extent of tunneling. Qualitative data that is typically noted by the wound care clinician during a wound assessment includes drainage amount, drainage color, drainage odor, tissue coloration, tissue texture, and relative tissue temperature. Qualitative data is collected visually or by touch.

The current most commonly used wound assessment procedure states that the greatest length, greatest width, and greatest depth of the wound are to be measured. The clinician uses his/her own judgment to determine the longest and widest points which are typically measured using a ruler.

Depth information is generally acquired using a cotton-tipped applicator and a ruler. The clinician again uses his/her own judgment to determine the deepest point in the wound. The cotton-tipped applicator is inserted into the deepest point of the wound and grasped such that the thumb marks the point at which the surface plane of the outer tissue intersects the applicator. The ruler is then used to measure the distance from the tip of the thumb to the tip of the applicator, indicating the depth of the wound Location measurements are typically referenced to an imaginary clock face which is oriented such that 6 o'clock is closest to the patient's feet. The angular extent of undermining is typically noted using the clock face method. For example undermining may extend from 1 o'clock to 5 o'clock.

The depth of the undermining is also measured using a cotton-tipped applicator in the same fashion as wound depth. Tunneling location is noted with reference to the clock face.

Tunneling depth is measured using a cotton-tipped applicator and ruler in the same fashion as wound depth.

The data acquisition methods described in the previous paragraphs have proven insufficient in many ways. First, the subjectivity involved with the visual determination of the longest, widest, and deepest points of the wound tends to result in large inconsistencies in the surface measurement data. This data is typically used to determine healing progress and, as a result, healing progress is frequently misinterpreted.

The use of rulers in making surface measurements has also been problematic. The relatively low resolution of the ruler does not provide adequate insight into new tissue development over time. For example if a ruler with 1 mm resolution was used to make a depth measurement of 1.0 cm then technically at least 0.5 mm of new tissue growth must occur before the next measurement for any healing progress to be recognized.

Also, the spongy texture of tissue makes it hard to rely on measurement instruments such as rulers or cotton tipped applicators to provide accurate and consistent data. The pressure applied while holding the measurement instruments down onto the tissue would have to be consistent between measurements in order for the measurements themselves to be consistent.

The positioning of the patient also tends to vary from measurement to measurement. Positioning the patient differently can result in stretching of the wound which distorts the wound differently with each position. This makes it extremely difficult to collect accurate and consistent measurement data.

There are several other factors that contribute to the inconstancy and inaccuracy of the data collected using currently accepted techniques. These factors include positioning and referencing of the clock face to determine tunneling location and angular extent of undermining, visually acquiring and interpreting tissue coloration and texture, and visually acquiring and interpreting drainage coloration and amount.

The data collected from the wound is analyzed to classify the wound and determine the most effective plan of care. It's safe to say that inaccurate data will result in inaccurate analysis results. Even with accurate data, the analysis techniques used to classify the wound and determine the most effective plan of care have proven inconsistent between clinicians. Clinical experience and academic background of the performing clinician tend to be key factors in how accurate the analysis results are.

The classification of the wound is determined by wound thickness, wound location, wound shape, drainage, odor, tissue coloration, tissue temperature, and tissue types present. Throughout the wound assessment, the clinician uses this information to "paint a picture" in their head by associating symptoms with patient or wound specific data. The ability to do this effectively relies heavily on the clinical experience and academic background of the clinician.

The most effective plan of care is determined based on the classification of the wound. If the wound is not classified properly, the most effective plan of care may not be implemented which can result in further injury to the patient, higher health care costs, and possibly loss of limb or life.

Currently, Applicant is aware of three prior art systems on the market which perform some, but not all, of the parts of the Wound Measurement and Tracking System of the present invention. "The Scout", sold by Woundvision, is an infrared and visible 2D imaging system. A visible camera is used to take high resolution images of the wound. The data processing software employs an edge detection algorithm to detect wound edges and determine length, width, and area measurements. A long-wave infrared imaging device allows the user to measure surface tissue temperature. This information is used to indicate areas where deep tissue injuries have occurred and where ulcers may be forming. The Scout does not provide 3D measurement capability, undermining measurement capability, or tunneling measurement capability. The Scout also does not provide tissue type analysis, wound classification analysis, or plan of care recommendation.

A device called "Silhouette", manufactured by Aranz Medical, is a 3D measurement and wound documentation system designed to be used at the point of care. The Silhouette measures area, depth, and volume of wounds along with healing progress in the form of new tissue growth. This company offers a secure internet accessible database that stores and consolidates the information obtained from the devices so that data can be shared with other clinicians. The Silhouette does not provide tunneling, undermining, or tissue temperature capabilities. The Silhouette also does not offer tissue type analysis, wound classification analysis, or plan of care recommendation A company called eKare incorporated has developed a 3D imaging and analysis system that acquires a color 3D image of the wound. The 3D image data is analyzed by a software application that determines maximum length, maximum depth, maximum width, wound perimeter, wound area, volume, and tissue types by percentage. The eKare system does not measure tunneling or undermining and does not classify the wound or provide a plan of care recommendation.

The Wound Measurement and Tracking System of the present invention addresses all of the deficiencies observed in prior art systems. Extensive research was done to determine exactly what the user needs are and those needs were propagated through the engineering design process. Applying the systems engineering process in the development of the WMTS has resulted in a system that ultimately meets the needs of the user as no prior art device can. Prior art devices typically only identify one key technology and search for an application. This means that they focus on finding a way to use the technology that they have and not on the needs of the users This results in user needs not being fully met as is the case with the three competitor products mentioned in the paragraphs above. For this reason, most wound care clinicians are not using any one of the competitor systems. Instead, the inaccurate, subjective, and inconsistent ruler/clock face techniques are still used by a large majority of wound care clinicians. This evidences a long felt need in the industry has still not been met.

Thus, the need in the art for a wound measurement and tracking device is clear and the objective of the present invention is to provide a structure and system that addresses these and other needs in the art as is more fully described hereafter.

SUMMARY OF THE INVENTION

Accordingly, a wound measurement and tracking system includes a surface measurement indicator where the surface measurement indicator is configured to collect wound information from a wound. A transmitter device is provided that is connected with the surface measurement indicator and is configured to transmit wound information to a data processor. A tunneling depth indicator is provided where the tunneling depth indicator measures tunneling and undermining of the wound. A transmitter device is connected with the tunneling depth indicator that is configured to transmit tunneling and undermining information from the wound to a data processor. And a data processor is provided that is conformed to connect with both of the transmitter devices where the data processor includes data processing software configured for comparison and analysis of wound information.

All terms used herein are given their common meaning.

According to another aspect, the wound includes a wound bed with a wound perimeter and a peri-wound area extending outward from the wound perimeter where the data processor is configured to create a 3 D model of the wound bed and the peri-wound area from the wound information.

In another aspect, the surface measurement indicator 3 D model also includes a model of tunneling location, undermining angular extent and surface temperature. In one aspect, the surface measurement indicator includes a 3D camera, an inductance sensor, a measurement on-off button for activation, and a signal processor.

In a further aspect, the tunneling depth indicator includes a user display device, a measurement on-off button, a measurement probe and a signal processor.

In one aspect, the tunneling depth indicator includes a removable covering configured to cover said measurement probe during use.

In another aspect, the measurement probe is configured with a capacitance sensor where the capacitance sensor measures change in capacitance with change of depth of the measurement probe in the wound.

In one aspect, the data processor includes several data processing modules for processing data and several databases where the databases include wound classification, plan of care, tissue type, patient file and user credential databases. In a further aspect, the data processing modules includes modules selected from a group consisting of: user interface, main, system self-test, access control, patient information, patient file management, user supplied assessment information, tunneling depth measurement, surface measurement indicator, tissue type analysis, healing progress, wound classification and plan of care recommendation modules.

According to another embodiment of the invention, a wound measurement and tracking method consists of:

a. providing a surface measurement indicator where the surface measurement indicator is configured to collect wound information from a wound with a wound bed; a transmitter device connected with the surface measurement indicator configured to transmit wound information to a data processor, a tunneling depth indicator where the tunneling depth indicator measures tunneling and undermining within a wound bed of the wound; a transmitter device connected with the tunneling depth indicator configured to transmit tunneling and undermining wound bed information from the wound to a data processor, and a data processor conformed to connect with both of the transmitter devices where the data processor includes data processing software configured for comparison and analysis of wound and wound bed information;

b. obtaining wound information and transmitting the wound information to the data processor;

c. obtaining tunneling and undermining information from the wound bed and transmitting the tunneling and undermining wound bed information to the data processor; and d. utilizing said data processing software to compare and analyze the wound and wound bed information.

In another aspect, the wound bed includes a wound perimeter and a peri-wound area extending outward from the wound perimeter where the data processor is configured to create a 3 D model of the wound bed and the peri-wound area from the wound information.

In one aspect, the surface measurement indicator 3 D model also includes a model of tunneling location, undermining angular extent and surface temperature.

In a further aspect, the tunneling depth indicator includes a user display device, a measurement on-off button, a measurement probe and a signal processor.

In another aspect, the tunneling depth indicator includes a removable covering configured to cover the measurement probe during use.

In one aspect, the measurement probe is configured with a capacitance sensor where the capacitance sensor measures change in capacitance with change of depth of the measurement probe in the wound.

In one aspect, the surface measurement indicator includes a 3D camera, an inductance sensor, a measurement on-off button for activation, and a signal processor.

In another aspect, the data processor includes a plurality of data processing modules for processing data and a plurality of databases wherein said databases include wound classification, plan of care, tissue type, patient file and user credential databases and further wherein said plurality of data processing modules includes modules selected from a group consisting of: user interface, main, system self-test, access control, patient information, patient file management, user supplied assessment information, tunneling depth measurement, surface measurement indicator, tissue type analysis, healing progress, wound classification and plan of care recommendation modules.

According to another embodiment of the invention, a wound measurement and tracking system consists of a surface measurement indicator where the surface measurement indicator is configured to collect wound information from a wound with a wound bed where the wound bed includes a wound perimeter and a peri-wound area extending outward from the wound perimeter where the surface measurement indicator includes video, infrared and inductance devices for capturing wound information. A transmitter device is connected with the surface measurement indicator and is configured to transmit wound information to a data processor. A tunneling depth indicator is provided where the tunneling depth indicator measures tunneling and undermining within a wound bed of wound where the tunneling depth indicator includes a user display device, a measurement on-off button, a measurement probe and a signal processor. A transmitter device is connected with the tunneling depth indicator and is configured to transmit tunneling and undermining wound bed information from the wound to a data processor. A data processor is provided and is conformed to connect with both the transmitter devices where the data processor includes data processing software configured for comparison and analysis of wound and wound bed information where the data processor is configured to create a 3 D model of the wound bed and the peri-wound area from the wound information.

In another aspect, the measurement probe is configured with a capacitance sensor where the capacitance sensor measures change in capacitance with change of depth of the measurement probe in the wound.

In one aspect, the surface measurement indicator includes a 3D camera, an inductance sensor, a measurement on-off button for activation, and a signal processor.

DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE INVENTION

Figure 1:
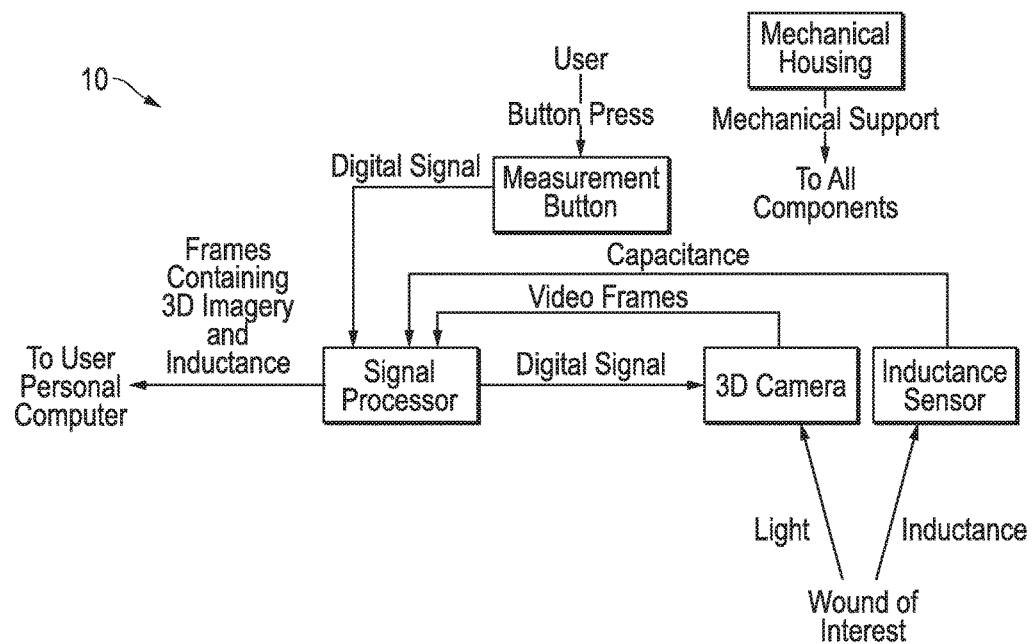
FIG. 1 is a block diagram of the Surface Measurement Indicator (SMI) device of the Wound Measurement and Tracking System of the present invention.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

For example, the specific sequence of the described process may be altered so that certain processes are conducted in parallel or independent, with other processes, to the extent that the processes are not dependent upon each other. Thus, the specific order of steps described herein is not to be considered implying a specific sequence of steps to perform the process. In alternative embodiments, one or more process steps may be implemented by a user assisted process and/or manually. Other alterations or modifications of the above processes are also contemplated.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

It should also be noted that a plurality of hardware devices, as well as a plurality of different structural components, may be utilized to implement the invention. Furthermore, and as described in subsequent paragraphs, the specific configurations illustrated in the drawings are intended to exemplify embodiments of the invention and that other alternative configurations are possible.

A preferred embodiment of the present invention is illustrated by way of example in FIGS. 1-14. After extensive independent research and consultation from subject matter experts, Applicant has determined that in order to meet the current market need, a system is needed that can be used throughout the entire wound assessment process. Applicant has identified three primary areas of focus during the assessment process around which the system has been developed. These high level system objectives are: Provide non-subjective, accurate, and consistent wound measurement capability; Provide non-subjective, consistent, and accurate data analysis capability that gives the user insight into the classification of the wound, the wound healing process, and the plan of care; and Provide wound care specific patient information management capability.

Applicant has developed a total wound care system that collects patient and wound specific data, analyzes the data, and recommends a plan of care based on the analysis. The Wound Measurement and Tracking System 10 of the present invention is comprised of two hand-held measurement devices and accompanying software. The first handheld measurement device, referred to as the "Surface Measurement Indicator" 12, (SMI) collects a color three dimensional model of the wound bed and peri-wound area, undermining angular extent, tunneling location, and surface tissue temperature. The second hand held measurement device, referred to as the "Tunneling Depth Indicator" 14, (TDI) collects highly accurate tunneling and undermining depth information. The accompanying software, referred to as the "Data Processing Software" provides a user interface which assists the user in creating new patient files, performing wound assessments, performing data analyses, and recommending the most effective plan of care. The software also contains a user authentication database which adheres to HIPAA regulations by keeping patient data secure from unauthorized users.

The SMI 12 is a handheld device that is used by the clinician to collect a color 3D model of the wound bed and peri-wound surfaces, tunneling location, undermining angular extent, and a surface tissue temperature model of the wound bed and peri-wound surfaces. The wound bed area is defined as the area within the perimeter of the wound. The peri-wound area is defined as the area outside of the wound perimeter. The peri-wound area extends outward from the wound perimeter and contains any structure, such as tunneling or undermining, associated with the wound of interest which is outside of the wound perimeter.

Figure 2:
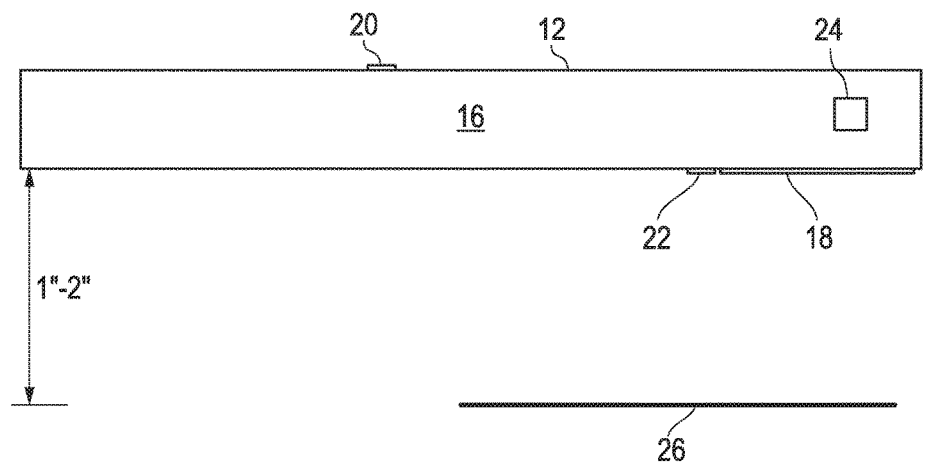
FIG. 2 is a side view of the SMI device of FIG. 1.

As illustrated in FIG. 2, the SMI 12 is comprised of a mechanical housing 16, a depth of focus 3D camera 18, a measurement button 20, an inductance sensor 22, and a signal processor 24. FIG. 1 shows a physical block diagram of the SMI device 12.

The physical outer dimensions of the SMI mechanical housing 16 are approximately 2"×2"×9". The SMI 12 device is designed to be held at one end in the hand of the user (not shown) and moved randomly over the wound of interest while collecting data. The random movement of the device will be referred to from this point forward as a "scan" or "scanning". The focal plane of the 3D camera 18 and the inductance sensor 20 are physically and approximately located on the same plane. The SMI 12 device is designed to be held such that this plane is 1" to 2" above the surface 26 to be measured.

The SMI 12 device collects frames of information from the wound. Each frame contains color three dimensional surface information and inductance information. If the device 12 is at the specified 1" to 2" height above the measurement surface 26, the physical dimensions of the measurement surface represented in each frame are approximately 1.5"×1.5". Frames of data are captured at a rate of fifteen frames per second, for example only and not by limitation, and multiple frames are captured as the user scans the measurement surface 26 with the SMI 12 device. To perform a scan, the user presses the measurement button 20 and moves the device 12 parallel to the measurement surface 26 while keeping the device 12 within the specified height above the measurement surface 26. The user continues this movement until the entire area of interest has been measured.

As illustrated in FIG. 1, when the user presses the measurement button 20, a measurement command is sent to the signal processor 24. The signal processor 24 activates the 3D camera 18 which begins capturing 3D frames from the wound surface 26. At the same time the inductance sensor 22 measures inductance. The 3D image and the inductance measurement are captured by the signal processor 24 which packages the data into a frame. The inductance sensor 24 measures inductance as the user scans the wound of interest. The inductance measurement data is also acquired by the signal processor 24.

The signal processor 24 sends the data to a personal computer (not shown) on which the data processing software is running.

The data processing software uses the inductance data along with the 3 dimensional model data to create a topological image of measured inductance. Relative changes in inductance indicate discontinuities in the tissue such as undermining or tunneling. It is from this data that undermining angular extent and tunneling location is derived. A more detailed explanation of the data processing software is given in later sections. Again, a mechanical drawing of the SMI 12 device is shown in FIG. 2.

Figure 4:
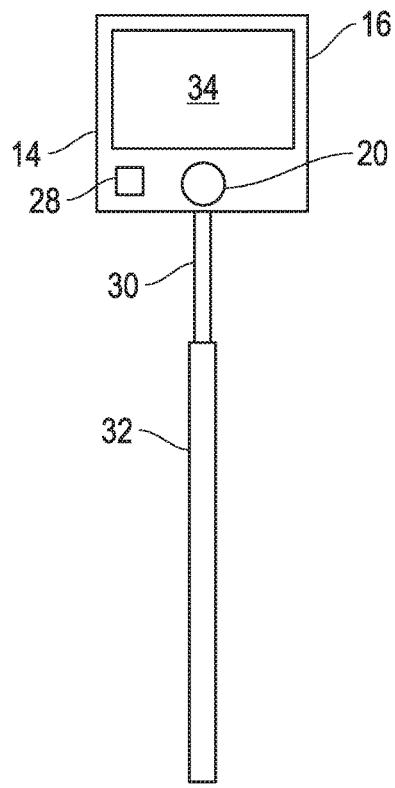
FIG. 4 is a side view of the TDI device of FIG. 3.

Referring to FIG. 4, the Tunneling Depth Indicator (TDI) 14 is a handheld device used to measure the depth of tunneling or undermining within the wound bed or peri-wound areas. Tunneling is described as a narrow passage that begins in or near the wound bed area and extends down or outward. Undermining is described as a relatively wide separation between two layers of tissue that typically begins at the wound perimeter and extends outward away from the center of the wound bed. Undermining typically occurs in the form of a cavity under the outer layers of tissue.

Figure 3:
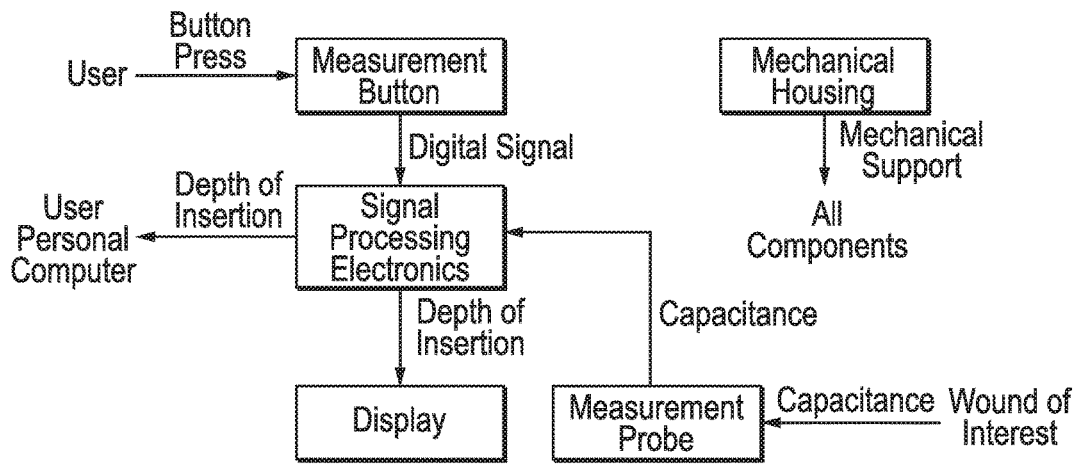
FIG. 3 is a block diagram of the Tunneling Depth Indicator (TDI) device of the Wound Measurement and Tracking System of the present invention.

The TDI 14 is comprised of a mechanical housing 16, a printed circuit board 28, and a replaceable sterile covering 32 for the measurement probe 30. The printed circuit board 28 contains a user display 34, measurement button 20, measurement probe 30, and signal processing electronics. The printed circuit board 28 is contained within the mechanical housing 16. FIG. 3 is a physical block diagram of the TDI 14 device.

To use the TDI 14, as shown in FIG. 3, the user presses the measurement button 20 and then immediately inserts the measurement probe 30 into the tunneling or undermining of a wound (Not shown). The user inserts the measurement probe 30 until it is physically stopped at the backside of the tunneling or undermining. The TDI 14 measurement probe 30 is a capacitance sensor that measures the change in capacitance as the probe 30 is inserted into the tunneling or undermining. The signal processing electronics interpret the change in capacitance as depth of probe 30 insertion. The signal processing electronics send the depth of insertion to the user display 34 giving the user a visual indication of the tunneling or undermining depth.

The signal processing electronics also send the depth of insertion information to a personal computer (not shown) where it is used within the data processing software.

The display 34, measurement button 20, and signal processing electronics are physically located on one end of the TDI printed circuit board 28. The physical dimensions of this end of the printed circuit board 28, for example only, without the measurement probe 30, are approximately 2"×2". The measurement probe 30 extends away from the display end of the printed circuit board 28. The outer physical dimensions of the measurement probe 30 are, for example only, approximately 0.08"×0.08"×5.5".

The TDI 14 device also includes a sterile plastic covering 32, preferably, that fits over the measurement probe 30. This plastic covering 32 is held in place by a friction lock device for example only (not shown) and is discarded after the patient measurement is complete. A new sterile covering 32 is put in place before each individual patient measurement. FIG. 4 is a mechanical drawing of the TDI 14 device.

The "WMTS" data processing software runs on a personal computer into which the handheld measurement devices are connected. There are 13 individual software modules included in the data processing software. They are:
1. User Interface
2. Main Module
3. System Self-Test Module
4. Access Control Module
5. Patient Information Module
6. Patient File Management Module
7. User Supplied Assessment Information Module
8. Tunneling Depth Measurement Module
9. SMI Scan Module
10. Tissue Type Analysis Module
11. Healing Progress Analysis Module
12. Wound Classification Module
13. Plan of Care Recommendation Module There are also five small databases included within the WMTS data processing software. They are:
1. Wound Classification Database
2. Plan of Care Database
3. Tissue Type Database
4. Patient File Database
5. User Credential Database As discussed hereafter in reference to FIGS. 5-14, these databases are stored on the local hard drive and contain data that is typically used in comparison algorithms within the 13 software modules listed above.

The user interface accepts user directives from other software modules and displays them to the users. User directives are directions intended for the user that assist the user through the wound assessment process. The user interface accepts system commands from the user. System commands are sent from the user interface to other software modules and command the system to perform different tasks.

The WMTS Main Module is responsible for process and data flow within the data processing software component. The WMTS Main Module interfaces with every other module and almost all other modules are accessed through the main module.

Figure 5:
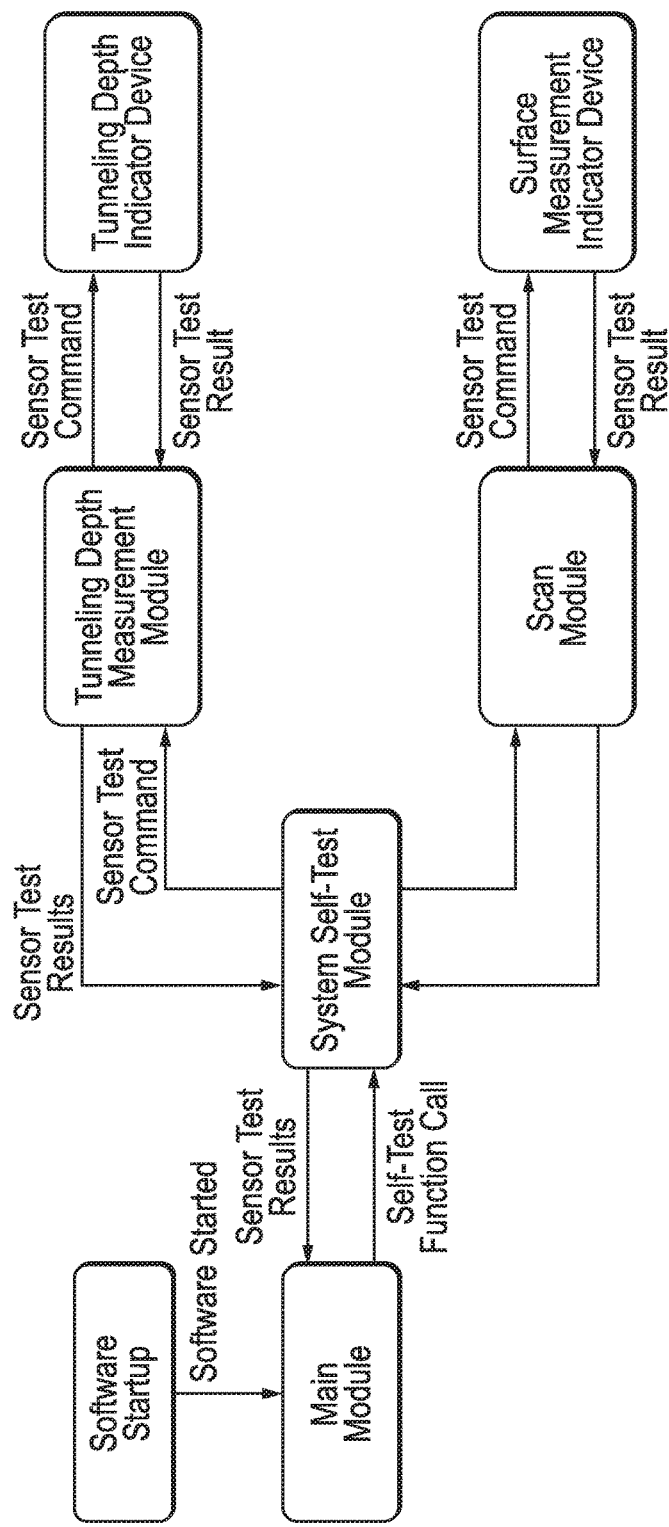
FIG. 5 is a flow diagram for the self-test process of the system.

Upon software startup, the main module initiates the self-test functionality by calling the system self-test function from the self-test module. The self-test module calls the sensor test functions within each of the measurement modules. Each of the sensor test functions provide outputs indicating the results of the associated sensor test. The self-test module sends the sensor test results back to the main module which then sends system status to the user interface for display. A data flow diagram showing how data flows within the system self-test process is shown in FIG. 5.

Upon completion of the system self-test, the main module calls the access control function from within the access control module. The access control module sends the user directives and user controls to the user interface for display. The main module accepts the user credentials from the user interface. The main module sends the user credentials to the data storage subsystem where they are verified. If the credentials are verified, the data storage subsystem sends the allow access signal back to the main module.

If the credentials cannot be verified, the data storage subsystem sends the deny access signal to the main module. Upon receiving the allow/deny access signal, the main module either allows the user to access other system functionality or asks the user to re-enter the credentials.

Figure 6:
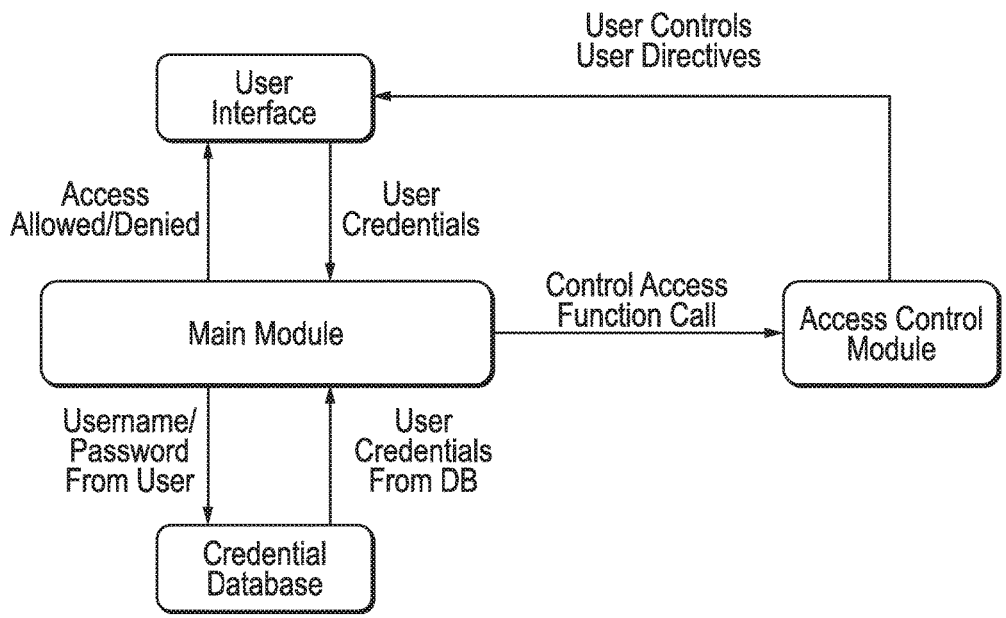
FIG. 6 is a flow diagram of the access control process of the system.

The main module allows the user to access other system functionality by sending user controls to the user interface that allow the user to input patient information, perform a wound assessment, analyze wound assessment data, or get a plan of care recommendation. A data flow diagram showing how data flows within the access control process is shown in FIG. 6.

If the user activates the input patient information command, the main module receives this command from the user interface and calls the input patient information function within the patient information management module. The patient information module then sends user controls and user directives to the user interface. The user can then use the controls to input patient information such as patient name, height, weight, wound culture results, blood lab results, socioeconomic state, and available caregivers.

Figure 7:
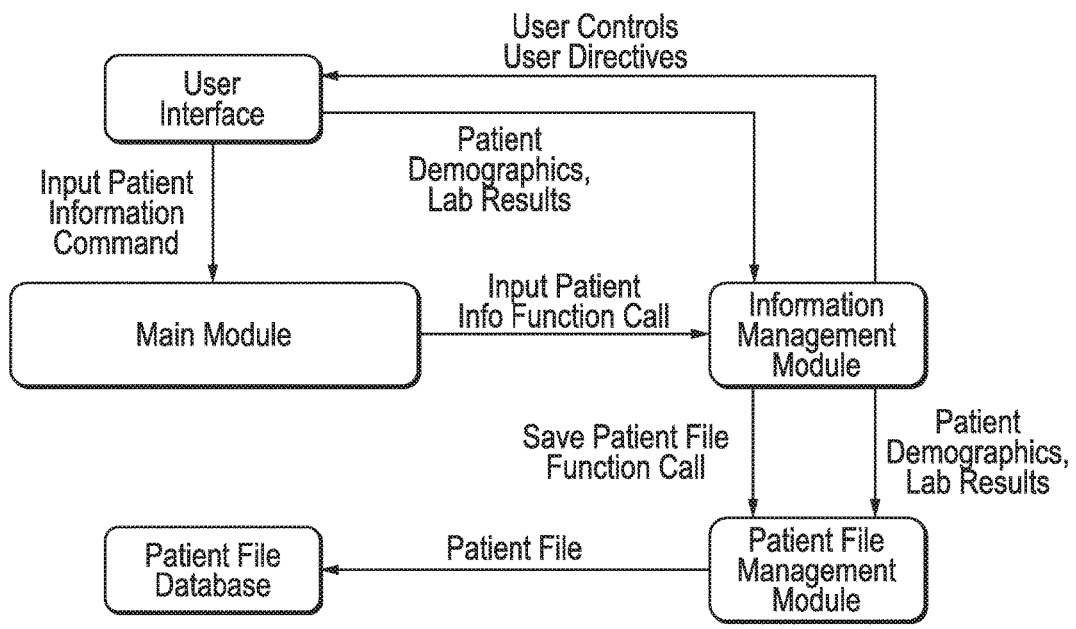
FIG. 7 is a flow diagram of the patient information management process of the system.

The patient information input function then calls the save patient file function within the patient file management module. The inputs to the save patient file function are the patient information received from the user. The save patient file function saves the patient file within the patient file database. FIG. 7 is a data flow diagram showing how data flows within the patient information management process.

If the user activates the perform wound assessment user control, the main module accepts the command and calls the input wound assessment data function within the user supplied assessment information module. The user supplied assessment information module sends user directives and user controls to the user interface. The user can use the controls to input assessment information such as wound ID number, head to toe assessment information, drainage type, drainage amount, drainage odor, wound type, wound location, and patient position.

Figure 8:
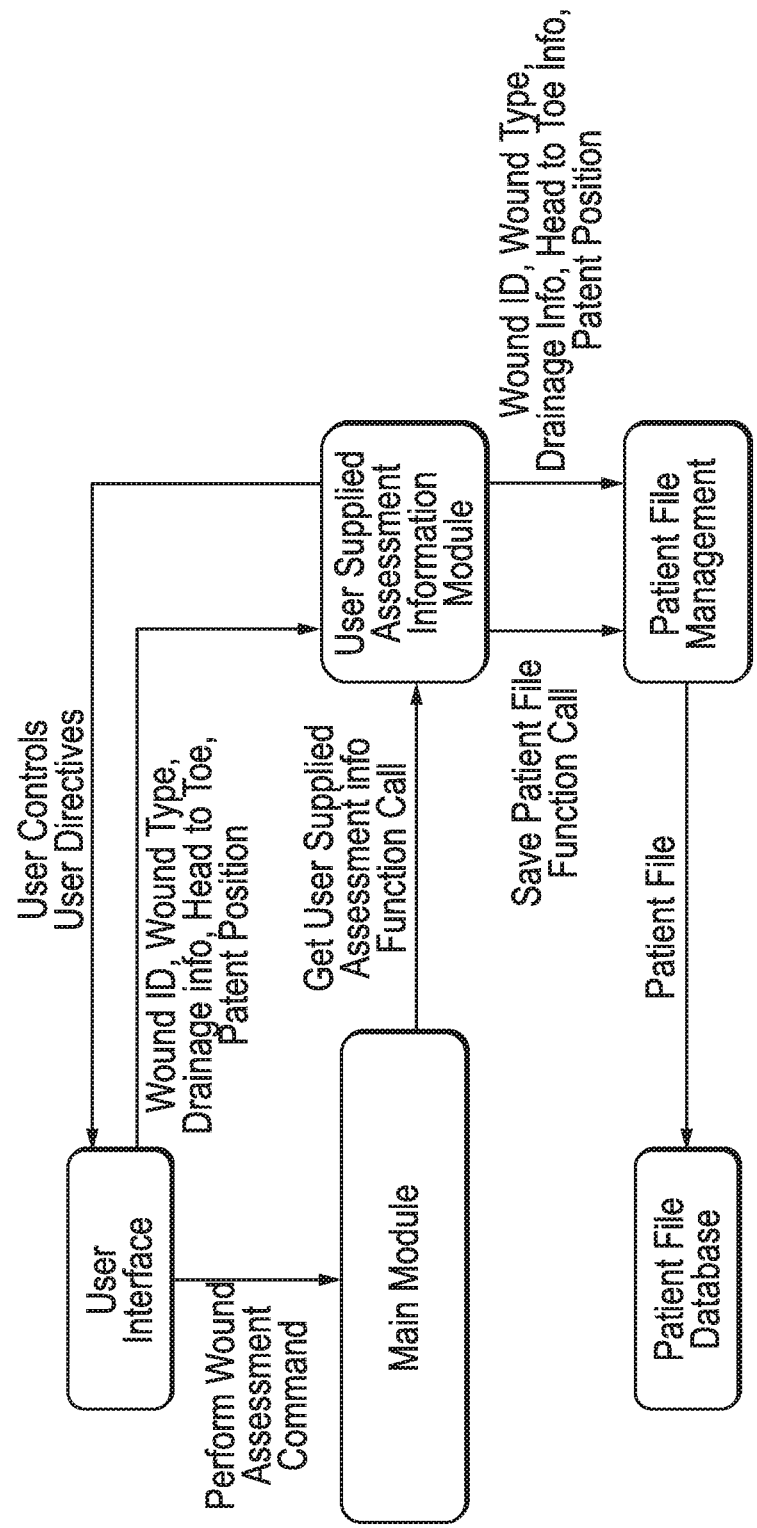
FIG. 8 is a flow diagram of the user supplied assessment information process of the system.

The user supplied assessment information module sends the user supplied assessment information to the patient file management module where it is saved into the patient file database. FIG. 8 is a data flow diagram showing how information flows within the user supplied assessment information process.

Upon completing the patient information input step, the main module will begin the process of gathering system supplied measurement information. The main module will call functions within the SMI Scan module. The SMI Scan module will send user directives and user controls to the user interface module. The user can then use the controls to indicate that they are ready to perform an SMI scan.

Upon receiving this indication, the main module will call the make SMI scan function within the SMI Scan module. The SMI Scan module will then enter a state in which it is ready to receive data frames from the SMI device. The user then performs an SMI scan by pressing the measurement button on the SMI device and moving the device over the measurement surface. The SMI data frames are then sent from the SMI device to the SMI Scan module where they are processed to produce tissue coloration, tissue temperature, undermining angular extent, tunneling location, surface length, surface width and surface depth data.

Figure 9:
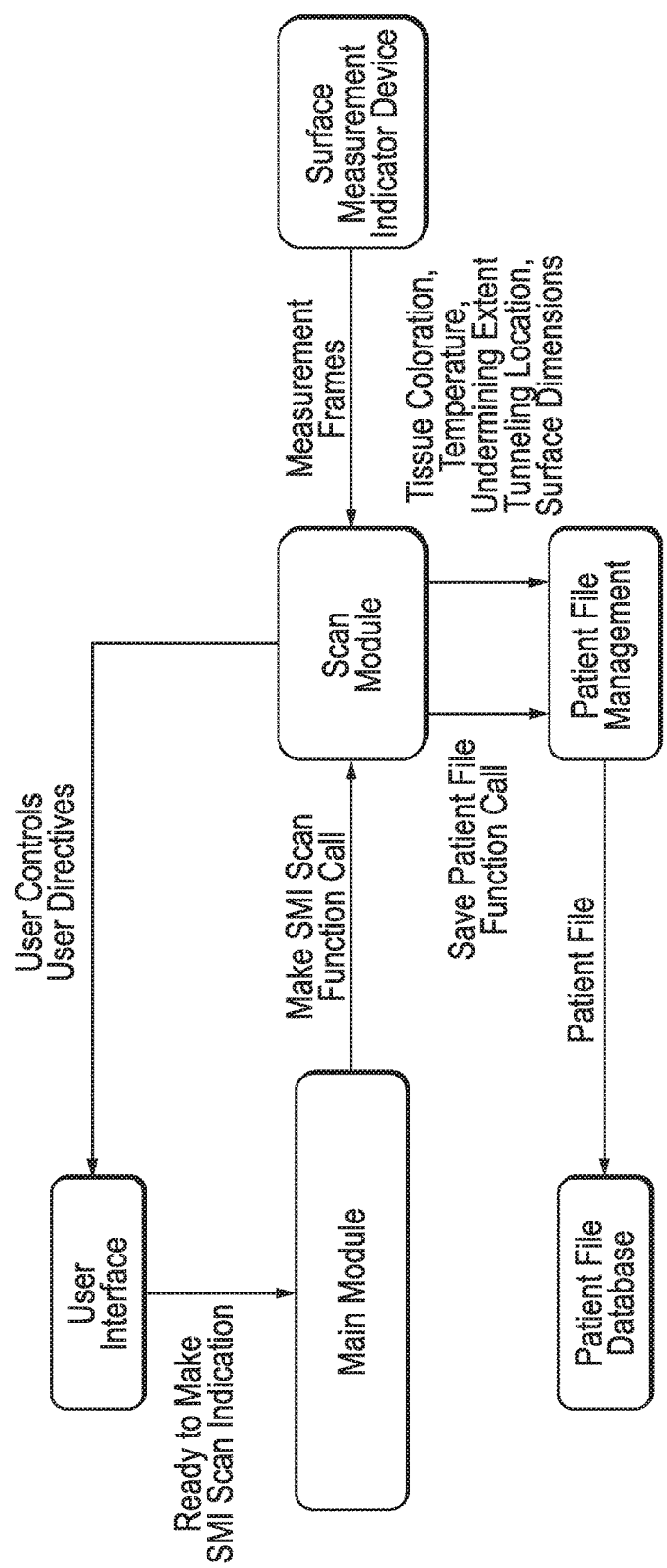
FIG. 9 is f flow diagram of the SMI scan process of the system.

All of the processed data along with the 3D model are sent to the patient file management module where it is written to the patient file and saved within the patient file database. FIG. 9 is a data flow diagram showing how data flows within the SMI Scan process.

After completing the SMI scan, the main module will call functions within the tunneling depth measurement module. The tunneling depth measurement module will send user directives and controls to the user interface where they are displayed to the user. The user can use the controls to indicate to the system that the user is ready to perform a tunneling depth measurement.

Upon receiving this indication, the main module will call the make tunneling depth measurement function within the tunneling depth measurement module. The tunneling depth measurement module will then enter a state in which it is ready to receive tunneling depth information.

Figure 10:
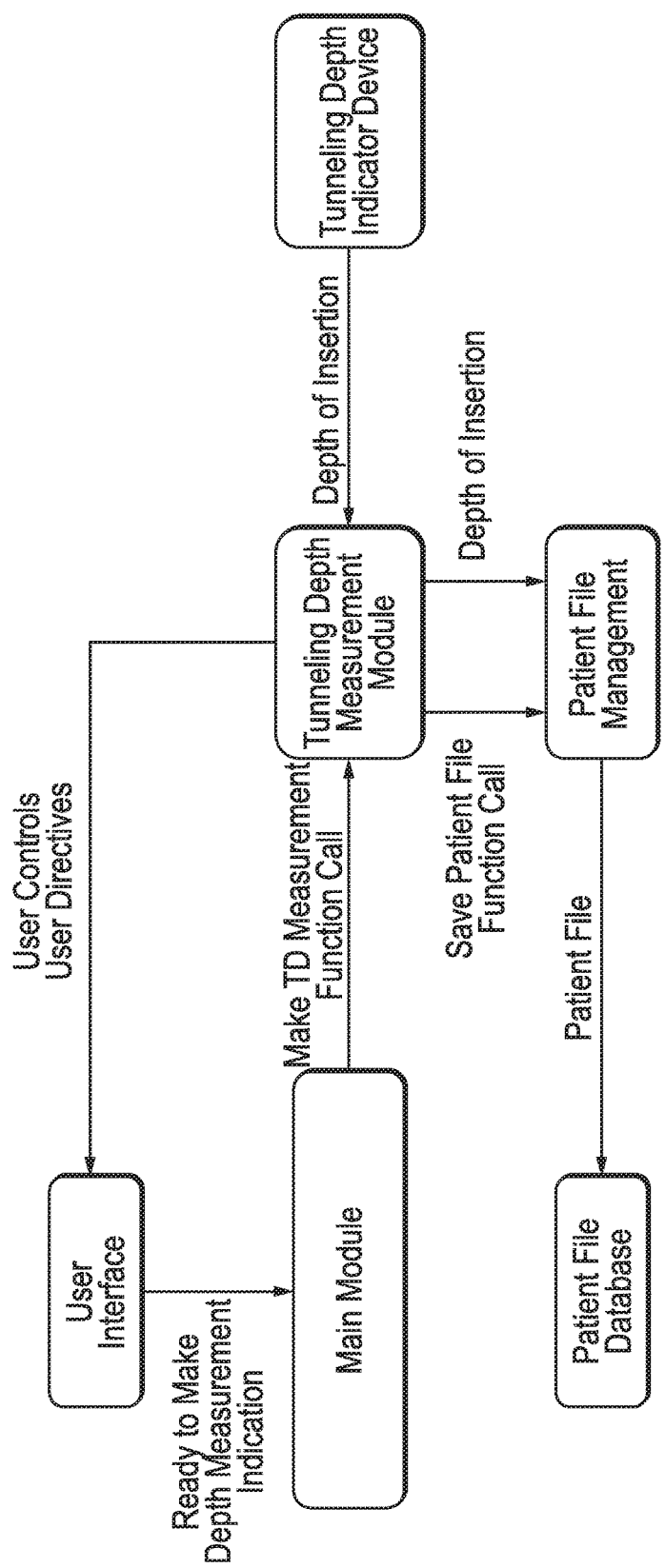
FIG. 10 is a flow diagram of the TDI measurement process of the system.

The user then presses the measurement button on the TDI device and inserts the measurement probe into the wound tunnel or undermining. The depth of insertion data is sent from the TDI device back to the Tunneling Depth Measurement module. The Tunneling Depth Measurement module sends the tunneling depth to the patient file management module where it is written to the patient file and saved within the patient file database. FIG. 10 is a data flow diagram showing how data flows within the tunneling depth measurement process.

After all wound assessment information has been collected and saved within the patient file, the user can choose to command the system to perform data analysis. If the user commands the system to perform tissue type analysis, the main module receives this command and calls the perform tissue type analysis function within the tissue type analysis module. The tissue type analysis module sends user directives and controls to the user interface that allow the user to input patient name and wound id information. The tissue type analysis module receives this information and accesses the patient file associated with the patient name and then accesses the tissue coloration and tissue temperature data associated with the wound ID through the patient file management module.

Figure 11:
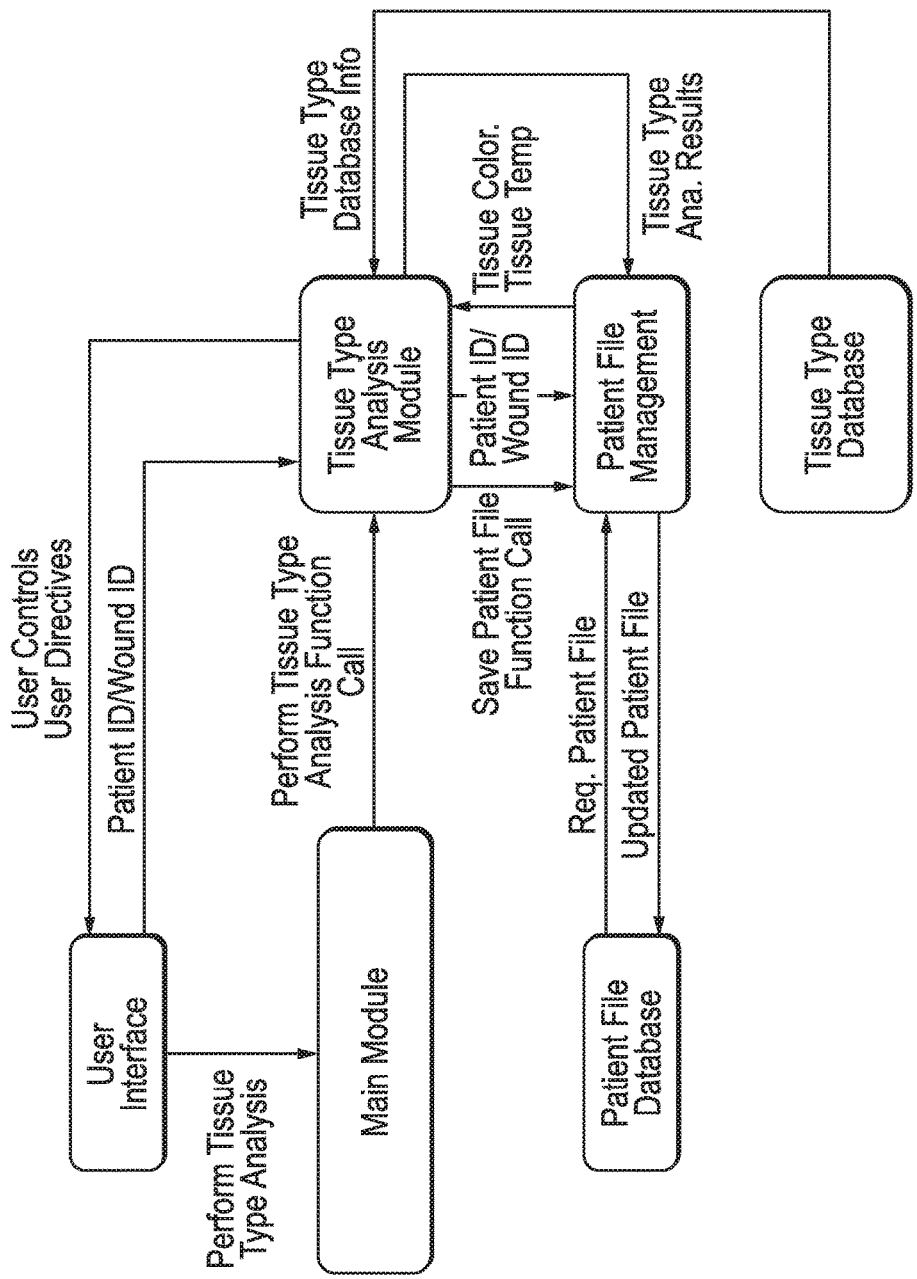
FIG. 11 is a flow diagram of the tissue type analysis process of the system.

The perform tissue type analysis function uses tissue temperature, tissue coloration, and temp/color location to determine the tissue types and tissue type locations within the wound bed and peri-wound area. The perform tissue type analysis function sends the tissue type and location information to the patient file management module where it is stored in the patient file. FIG. 11 is a data flow diagram showing how data flows within the tissue type analysis process.

If the user commands the system to perform wound classification analysis, the main module calls the perform wound classification function within the wound classification module. The wound classification function sends user directives and controls to the user interface allowing the user to input patient identification information and wound ID. The wound classification module then accesses the patient file associated with the patient information and gathers assessment data associated with the wound ID.

Figure 12:
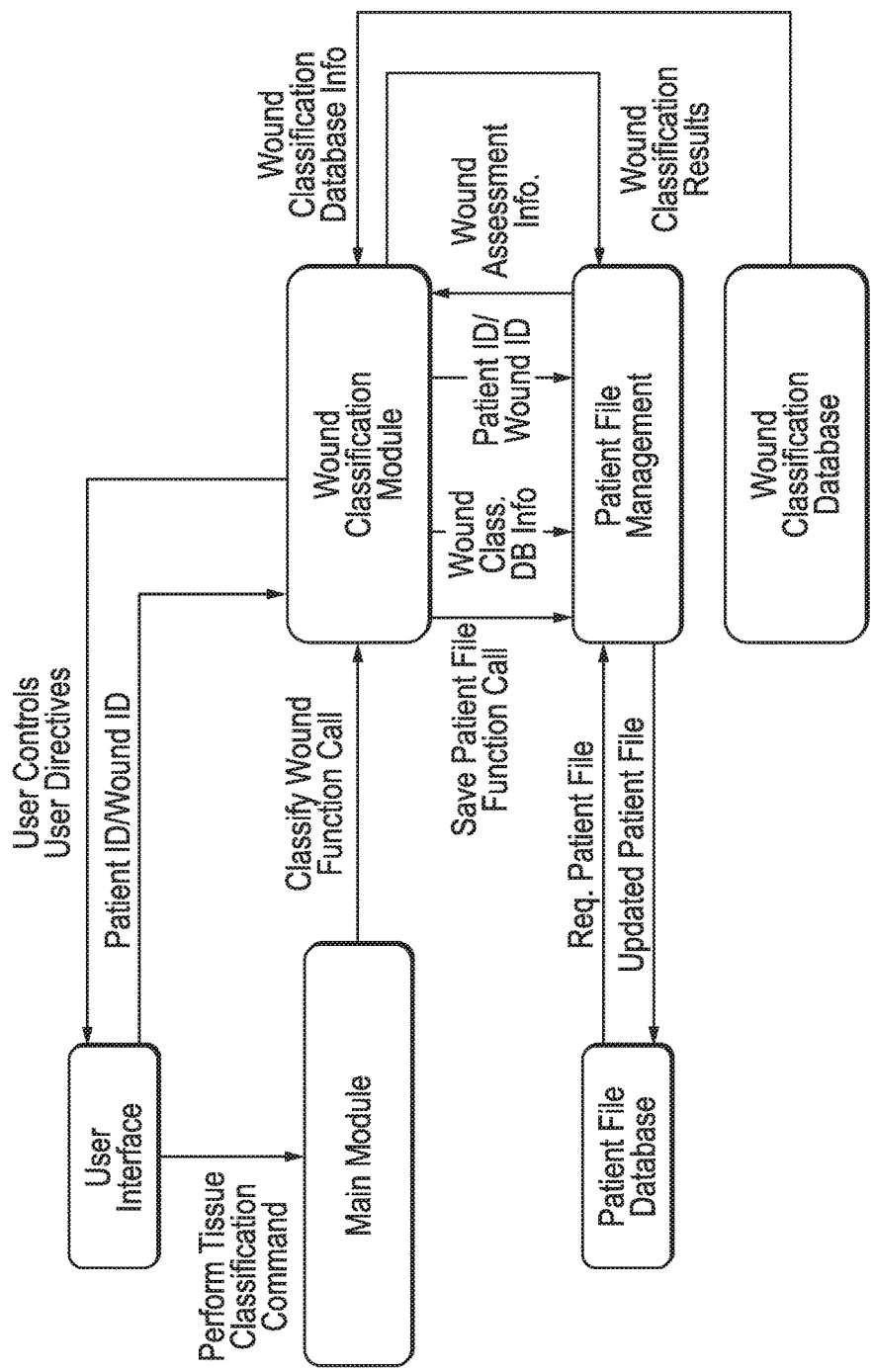
FIG. 12 is a flow diagram of the wound classification process of the system.

The information gathered includes the wound type, wound location, drainage information, tissue type analysis results, and surface dimension measurement data. The wound classification function then accesses the wound classification data base and compares the information in the data base with the information in the patient file to determine a wound classification. The wound classification results are sent to the patient file management module where they are saved to the patient file. FIG. 12 is a data flow diagram showing how data flows within the wound classification process.

If the user commands the system to recommend a plan of care, the main module receives this command and calls the recommend plan of care function within the plan of care recommendation module. The plan of care recommendation module sends user directives and controls to the user interface that allow the user to input patient identification information and wound ID. The plan of care recommendation function uses the patient identification information to access the patient file and the wound ID information to gather the wound type and classification for the wound of interest. The recommend plan of care function accesses the plan of care database and compares the information in the database to the information from the patient file to determine the proper plan of care recommendation. The recommendation is sent back to the user interface along with controls that allow the user to input the plan of care that was actually implemented.

Figure 13:
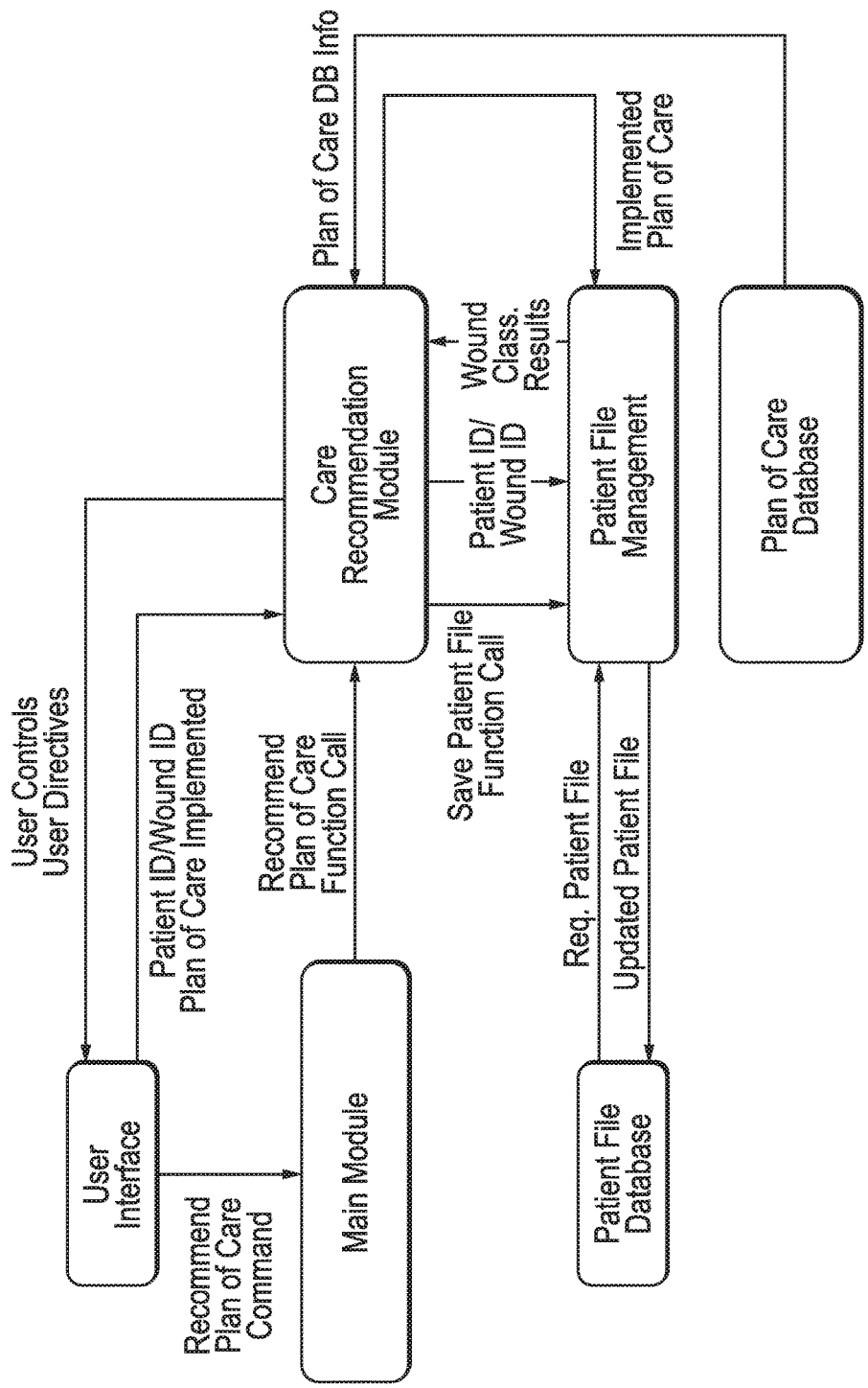
FIG. 13 is a flow diagram of the plan of care recommendation process of the system.

The plan of care recommendation module sends the implemented plan of care to the patient file management module where it is saved within the patient file. FIG. 13 is a data flow diagram showing how data flows within the plan of care recommendation process.

If the user commands the system to perform healing progress analysis, the main module receives this command and calls the perform healing progress analysis function. The healing progress analysis module sends user directives and controls to the user interface that allow the user to input patient identification information, wound ID, and analysis time span. The healing progress analysis function accesses the associated patient file and gathers 3D models, tissue type information, tunneling measurements, and undermining measurements for the wound of interest for every date within the analysis time span.

Figure 14:
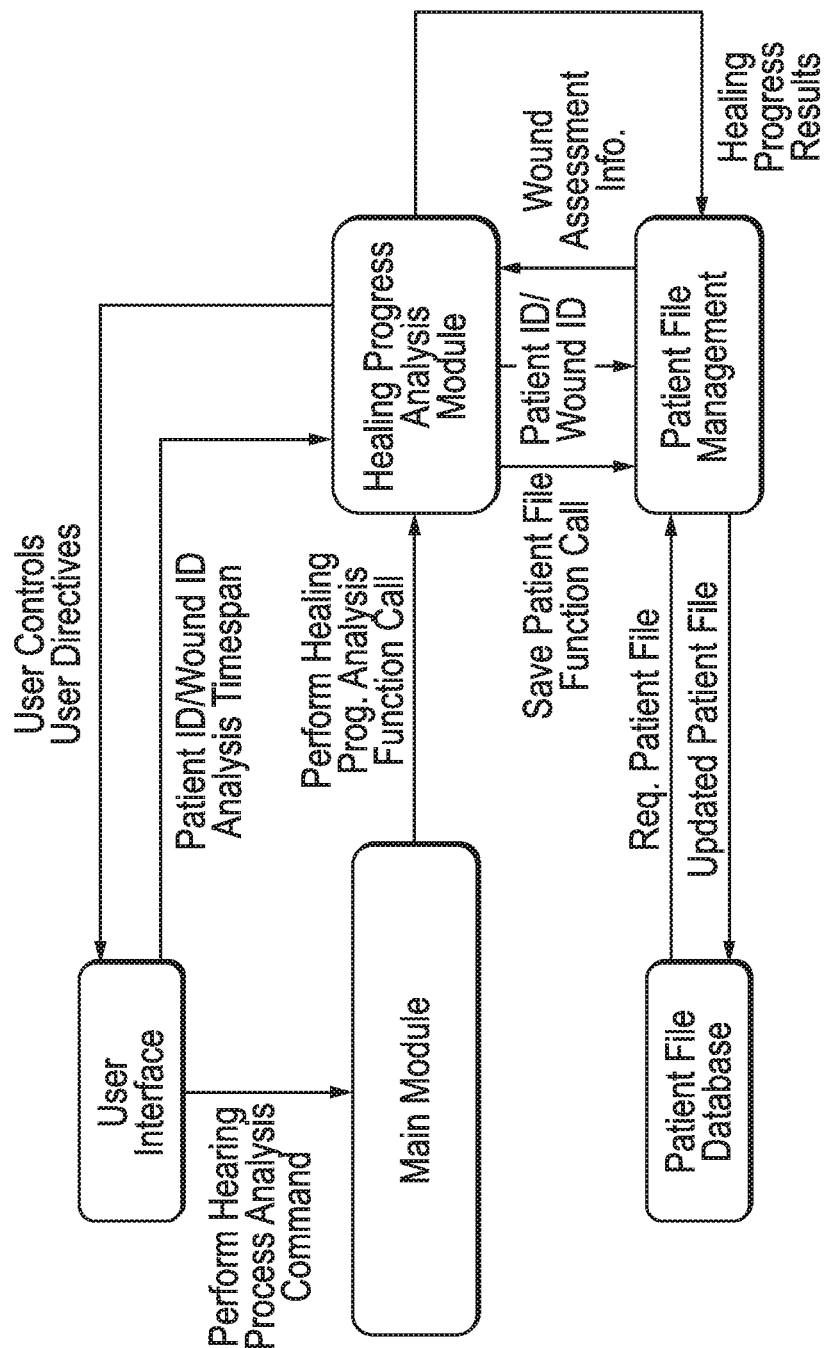
FIG. 14 is a flow diagram of the healing progress analysis process of the system.

The perform healing progress analysis function then uses this information to determine the relative healing progress of the wound for each date. The healing progress analysis function the sends this information to the patient file management module where it is saved to the patient file. FIG. 14 is a data flow diagram showing how data flows within the healing progress analysis process.

The patient file management module receives data from the main module, writes the data to the associated patient file, and saves the patient file within the patient file database. The patient file module also accesses patient files within the patient file database, parses the files, and provides access to the information for other software modules.

The wound classification database is where wound classification information, which is used within the data analysis functionality, is stored. For example, the system classifies lacerations based on wound depth and tissue types present within the wound bed. If a laceration is being assessed, the system would access information pertaining to lacerations from the wound classification database. This information would be passed from the database to the WMTS data processing software module that requires the information The plan of care database contains information pertaining to the plan of care recommendations associated with each wound type and classification. For example, if the wound classification software module determined that the wound type was laceration and the classification was partial thickness, specific plan of care recommendations would be accessed from the database based on this information. The plan of care recommendations pertaining to a partial thickness laceration would then be passed from the plan of care database to the plan of care recommendation software module.

The tissue type database contains tissue coloration and temperature data pertaining to each tissue type. Tissue type information is compared to wound assessment data and the comparison results are used to determine the tissue types present within the wound bed All of the information collected during the wound assessment process is ultimately written to a patient file along with analysis results. The patient files are stored in the patient file database.

The user credential database contains information used for access control functionality. The user credential information from the database is compared to the user credential information entered by the user through the user interface. Access to patient files is allowed or denied based on comparison results.

In sum, inter alia, and for example only and not by limitation, key advantages of the present invention are:
1. The ability to make accurate and consistent undermining measurements
2. The ability to make accurate and consistent tunneling measurements
3. The ability to completely manage wound-specific patient information
4. The ability to classify wound types based on tissue type analysis and other acquired data
5. The ability to recommend the most effective plan of care based on the wound type
6. The ability to use the tissue type analysis results along with 3D measurement data to determine healing progress in every specific area of the wound
7. The WMTS is fully capable of providing a more thorough wound assessment than can be accomplished using common assessment techniques or competitor systems The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. A wound measurement and tracking system comprising:
   a. a surface measurement indicator wherein said surface measurement indicator is configured to collect wound information from a non-contact position above a wound;
   b. a transmitter device connected with said surface measurement indicator configured to transmit wound information to a data processor;
   c. a tunneling depth indicator with a measurement probe wherein said tunneling depth indicator measures tunneling and undermining of said wound and wherein said measurement probe includes a capacitance sensor wherein said capacitance sensor measures change in capacitance along said measurement probe with change of depth of said measurement probe in said wound;
   d. a transmitter device connected with said tunneling depth indicator configured to transmit tunneling and undermining information from said wound to a data processor, and e. a data processor conformed to connect with both said transmitter devices wherein said data processor includes data processing software configured for comparison and analysis of wound information for classification and effective treatment of said wound.

2. The apparatus of claim 1 wherein said wound includes a wound bed with a wound perimeter and a peri-wound area extending outward from said wound perimeter wherein said data processor is configured to create a 3 D model of the wound bed and the peri-wound area from said wound information.

3. The apparatus of claim 2 wherein said surface measurement indicator 3 D model also includes a model of tunneling location, undermining angular extent and surface temperature.

4. The apparatus of claim 3 wherein said surface measurement indicator includes a 3D camera, an inductance sensor, a measurement on-off button for activation, and a signal processor.

5. The apparatus of claim 1 wherein said tunneling depth indicator includes a user display device, a measurement on-off button, a measurement probe and a signal processor.

6. The apparatus of claim 5 wherein said tunneling depth indicator includes a removable covering configured to cover said measurement probe during use.

7. The apparatus of claim 1 wherein said data processor includes a plurality of data processing modules for processing data and a plurality of databases wherein said databases include wound classification, plan of care, tissue type, patient file and user credential databases.

8. The apparatus of claim 7 wherein said plurality of data processing modules includes modules selected from a group consisting of: user interface, main, system self-test, access control, patient information, patient file management, user supplied assessment information, tunneling depth measurement, surface measurement indicator, tissue type analysis, healing progress, wound classification and plan of care recommendation modules.

9. A wound measurement and tracking method comprising:
   a. providing a surface measurement indicator wherein said surface measurement indicator is configured to collect wound information from a non-contact position above a wound with a wound bed; a transmitter device connected with said surface measurement indicator configured to transmit wound information to a data processor; a tunneling depth indicator with a measurement probe wherein said tunneling depth indicator measures tunneling and undermining within a wound bed of said wound and wherein said measurement probe includes a capacitance sensor wherein said capacitance sensor measures change in capacitance along said measurement probe with change of depth of said measurement probe in said wound a transmitter device connected with said tunneling depth indicator configured to transmit tunneling and undermining wound bed information from said wound to a data processor; and a data processor conformed to connect with both said transmitter devices wherein said data processor includes data processing software configured for comparison and analysis of wound and wound bed information for classification and effective treatment of said wound;
   b. obtaining wound information and transmitting said wound information to said data processor;
   c. obtaining tunneling and undermining information from said wound bed and transmitting said tunneling and undermining wound bed information to said data processor; and
   d. utilizing said data processing software to compare and analyze said wound and wound bed information for classification and effective treatment of said wound.

10. The method of claim 9 wherein said wound bed includes a wound perimeter and a peri-wound area extending outward from said wound perimeter wherein said data processor is configured to create a 3 D model of the wound bed and the peri-wound area from said wound information.

11. The method of claim 10 wherein said surface measurement indicator 3 D model also includes a model of tunneling location, undermining angular extent and surface temperature.

12. The method of claim 9 wherein said tunneling depth indicator includes a user display device, a measurement on-off button, a measurement probe and a signal processor.

13. The method of claim 12 wherein said tunneling depth indicator includes a removable covering configured to cover said measurement probe during use.

14. The method of claim 9 wherein said surface measurement indicator includes a 3D camera, an inductance sensor, a measurement on-off button for activation, and a signal processor.

15. The method of claim 9 wherein said data processor includes a plurality of data processing modules for processing data and a plurality of databases wherein said databases include wound classification, plan of care, tissue type, patient file and user credential databases and further wherein said plurality of data processing modules includes modules selected from a group consisting of: user interface, main, system self-test, access control, patient information, patient file management, user supplied assessment information, tunneling depth measurement, surface measurement indicator, tissue type analysis, healing progress, wound classification and plan of care recommendation modules.

16. A wound measurement and tracking system comprising:
   a. a surface measurement indicator wherein said surface measurement indicator is configured to collect wound information from a non-contact position above a wound with a wound bed wherein said wound bed includes a wound perimeter and a peri-wound area extending outward from said wound perimeter wherein said surface measurement indicator includes video, infrared and inductance devices for capturing wound information;
   b. a transmitter device connected with said surface measurement indicator configured to transmit wound information to a data processor,
   c. a tunneling depth indicator wherein said tunneling depth indicator measures tunneling and undermining within a wound bed of said wound wherein said tunneling depth indicator includes a user display device, a measurement on-off button, a measurement probe and a signal processor and wherein said measurement probe includes a capacitance sensor wherein said capacitance sensor measures change in capacitance along said measurement probe with change of depth of said measurement probe in said wound;
   d. a transmitter device connected with said tunneling depth indicator configured to transmit tunneling and undermining wound bed information from said wound to a data processor; and e. a data processor conformed to connect with both said transmitter devices wherein said data processor includes data processing software configured for comparison and analysis of wound and wound bed information wherein said data processor is configured to create a 3 D model of the wound bed and the peri-wound area from said wound information.

17. The apparatus of claim 16 wherein said surface measurement indicator includes a 3D camera, an inductance sensor, a measurement on-off button for activation, and a signal processor.

* * * * *